United States Patent [19]

Pasarela

[11] 4,145,409
[45] Mar. 20, 1979

[54] ACARICIDAL RESIN COMPOSITION CONTAINING SPIRO[CYCLOPROPANE-1,-1'-INDENE]-2-CARBOXYLIC ACID, 3,3-DIMETHYL-, α-CYANO-M-PHENOXYBENZYL ESTER

[75] Inventor: Nunzio R. Pasarela, Bridgewater, N.J.

[73] Assignee: American Cyanamid Company, Stamford, Conn.

[21] Appl. No.: 918,173

[22] Filed: Jun. 22, 1978

Related U.S. Application Data

[63] Continuation-in-part of Ser. No. 750,041, Dec. 13, 1976, abandoned.

[51] Int. Cl.$^2$ .................... A01K 27/00; A01K 29/00; A01M 1/20
[52] U.S. Cl. ........................................ 424/16; 424/14; 424/28; 424/78; 119/156
[58] Field of Search .................. 424/14, 16, 28, 78; 119/156

[56] References Cited
U.S. PATENT DOCUMENTS 3,852,416  12/1974  Grubb et al. ..................... 424/14
3,904,746   9/1975  Aries ............................... 424/28

FOREIGN PATENT DOCUMENTS 2519126  11/1975  Fed. Rep. of Germany ............. 424/14
2237580   2/1975  France ............................. 424/28

OTHER PUBLICATIONS

Matthysse Search-Agriculture, 14(11):1-31 (1975), "Comparative Susceptibility of the Chorioptic Mange Mite, Northern Fowl Mite and Brown Dog Tick to Acaricides."

Primary Examiner—Shep K. Rose
Attorney, Agent, or Firm—Harry H. Kline

[57] ABSTRACT

The invention is novel acaricidal resin compositions containing spiro[cyclopropane-1,1'-indene]2-carboxylic acid, 3,3-dimethyl-, α-cyano-m-phenoxybenzyl ester. More particularly, this invention relates to flexible collars for controlling ticks on companion animals prepared from novel dry blended polyvinyl chloride resin compositions containing spiro[cyclopropane-1,1'-indene]-2-carboxylic acid, 3,3-dimethyl-, α-cyano-m-phenoxybenzyl ester and 15% to 25%, by weight, of a selected plasticizing agent.

8 Claims, No Drawings

ACARICIDAL RESIN COMPOSITION CONTAINING SPIRO[CYCLOPROPANE-1,-1'-INDENE]-2-CARBOXYLIC ACID, 3,3-DIMETHYL-, α-CYANO-M-PHENOXYBENZYL ESTER

This application is a continuation-in-part of my co-pending application, Ser. No. 750,041, filed Dec. 13, 1976, now abandoned.

The present invention relates to novel dry blended extrudable and extruded (and compression molded) polyvinyl chloride resin compositions containing a plasticizing agent and, as the essential active ingredient, an acaricidally effective amount of spiro[cyclopropane-1,1'-indene)]-2carboxylic acid, 3,3-dimethyl-, α-cyano-m-phenoxybenzyl ester, and characterized by extended residual acaricidal activity and low mammalian toxicity.

The compositions of the invention are generally prepared in the finished form of extruded (and/or compression molded) flexible sheets, strips, swatches and the like, and are particularly well suited to use in the manufacture of acariicidal collars for companion animals, particularly dogs and cats, and farm animals.

Spiro[cyclopropane-1,1'-indene]-2-carboxylic acid 3,3-dimethyl-, α-cyano-m-phenoxybenzyl ester is disclosed in U.S. Pat. No. 3,962,458 (1976) as a systemic insecticidal and acaricidal agent for treatment of homothermic animals. U.S. Pat. No. 3,966,959 (1976) discloses and claims the compound.

The polyvinyl chloride (PVC) resins which may be utilized in the preparation of compositions of this invention are solids at room temperature. They have a weight average molecular weight of from 60,000 to 280,000 and an inherent viscosity of from about 0.5 to 1.2 determined by A.S.T.A. Method D-1243-58T (Method A). In this method inherent viscosity is determined on a solution of 0.2 g of resin in 100 ml of cyclohexanone at 30° C.

In accordance with this invention, it has been found that resin compositions comprising a polyvinyl chloride resin having a weight average molecular weight of from 60,000 to 280,000 and preferably 80,000 to 230,000 and an inherent viscosity between about 0.5 to 1.2 and preferably between 0.67 and 1.07, from about 15% to 25% by weight of a plasticizer such as dioctyphathalate or octyl epoxytallate and from about 18% to 35% by weight and preferably about 30% by weight of spiro[-cyclopropane-1,1'-indene]-2-carboxylic acid, 3,3-dimethyl-, α-cyano-m-phenoxybenzyl ester are effective for the control of pests, particularly acarina such as *Dermacentor variabilis* and *Rhipicephalus sanguineus* which infest companion and farm animals.

Preferred compositions comprise about 30% by weight of spiro[cyclopropane-1,1'-indene]-2-carboxylic acid, 3,3-dimethyl-, α-cyano-m-phenoxybenzyl ester, 20 to 25% by weight of dioctylphthalate, — -such as di-noctylphthalate or di-(2-ethylhexyl)phthalate, plasticizing agent, 0.1% to 0.5% by weight of stearic acid lubricant, 0.5% to 1.5% by weight of Thermolite 831-di-n-octyltin maleate polymer which is a PVC heat stabilizing agent, and about 48% to 66% by weight of Diamond Alkali PVC resin with an inherent viscosity of about 0.80 (A.S.T.M. D-1243-58T (A)) and with as approximate weight average molecular weight of 120,000 (approximate number average molecular weight: 50,000).

More preferred compositions of this invention contain about 30% by weight of spiro[cyclopropane-1,1'indene]-2-carboxylic acid, 3,3-dimethyl-, α-cyanomphenoxybenzyl ester, about 15% to 20% by weight of octyl epoxytallate (FLEXOL ® EP-8; a product of Union Carbide) plasticizing agent, 0.1% to 0.5% by weight of stearic acid lubricant, 0.8% to 1.2% by weight of Thermolite 831-di-n-octyltin maleate polymer which is a PVC heat stabilizing agent, and 48% to 66% and preferably about 48% by weight of Diamond Alkali PVC 40 resin with an inherent viscosity of about 0.80 (A.S.T.M. D-1243-58T(A)) and with an approximate weight average molecular weight of 120,000 (approximate number average molecular weight: 50,000).

Colorants, selected from inorganic and organic pigments, may be added to the above compositions, if desired, to achieve a more pleasing eye appeal. Usually 0.1% to 2% by weight of a pigment suffices to impart the desired effect to the compositions. Addition of a pigment colorant is compensated for by adjusting the resin content accordingly. Suitable inorganic pigments may be selected from carbon black, titanium dioxide, cadmium yellow and the like, organic pigments may be selected from a large group of quinacridone, anthraquinone, alizarine and phthalocyanine type of pigments and mixtures thereof.

The dry blended extrudable (and/or compression molded) compositions of the invention are converted into sheets, strips, ribbons and the like, by dry blending the finely divided, solid, low molecular weight PVC resin with the stabilizer, plasticizer and lubricant (and a pigment colorant if desired) and incorporating the desired amount of spiro[cyclopropane 1,1'-indene]-2-carboxylic acid, 3,3-dimethyl-, α-cyano-m-phenoxybenzyl ester as the acaricidal agent.

When the mixture is thoroughly dry blended, it is charged to the extruder, and extruded (or compression molded) at a stock temperature of about 160° C. at the exit. In operation, it has been found it most desirable to operate at a relatively low temperature to avoid thermal degradation of the spiro[cyclopropane 1,1'-indene]-2-carboxylic acid, 3,3-dimethyl-, α-cyano-m-phenoxybenzyl ester acaricidal agent. The preferred stock extrusion (or compression molding) temperature is between about 150° C. to 180° C.

The extrudate (or mold) from this process is obtained in the form of a flexible plastic strip or sheet, which is readily fashioned into collars for companion animals or farm animals. Extruded strips simply require the addition of a buckle or other fastening means to complete the collar. Sheets, may, of course, be cut into strips to which a buckling device may be appended and a collar prepared; or they may be cut into strips and coated on one side with adhesive such that the strips can be secured to the inside of a conventional collar.

Advantageously, the compositions of this invention have a very low mammalian toxicity. They have not been found to cause dermatitis on dogs, cats and the like when used in contact with the animals coat for an extended period of time. Moreover, they have been found to be effective up to 12 weeks for the control of ticks on the animals, and do not show diminished activity over this period of time.

Although the novel resin-acaricide compositions of the present invention provide lasting control only for ticks infesting companion animals, to achieve simultaneous control of fleas such as *Ctenocephalides canis* and *Ctenocephalides felis,* they may be combined physically with resin-siphonaptericidal compositions such as described in the J. P. Milionis et al., U.S. Pat. No.

4,041,151 issued Aug. 9, 1977, which relates to PVC-0,0,0,', 0 '-tetramethyl 0,0'-thiodi-p-phenylene phosphorothioate compositions.

Thus animal collars may be prepared by laminating two PVC resin strips side by side, one containing the acaricide and the other the siphonaptericide, respectively; and attaching a buckle or some other suitable fastening device thereto. Alternatively, strands of the resin strips may be woven into ribbons or suitable widths, and formed into animal collars. Animal collars thus prepared, would, obviously provide lasting and effective protection for companion animals against ticks and fleas, in addition, such a collar would have substantial aesthetic value.

The following non-limiting examples serve to further illustrate the invention.

EXAMPLE 1

Preparation of a PVC-Spiro[cyclopropane-1,1'-indene]-2-carboxylic acid, 3,3-dimethyl-, α-cyano-m-phenoxybenzyl ester composition Diamond PVC 40 resin (48.9 g), inherent viscosity approximately 0.80 as determined by A.S.T.M. D-1243-58T (Method A), approximate weight average molecular weight 120,000 (approximate number average molecular weight 50,000), stearic acid (0.24 g), octyl epoxytallate (FLEXOL ® EP-8; 20.0 g), 1.0 g. Thermolite 831-di-n-octyltin maleate polymer PVC heat stabilizing agent and technical spiro[cyclopropane-1,1'-indene]-2carboxylic acid, 3,3-dimethyl-, α-cyano-m-phenoxybenzyl ester (30.0 g — 82.5% pure, 24.75 g real) are mixed and thoroughly blended, and sheeted on a 143° C. two-roll rubber mill. The stock is mixed for 5 minutes by cutting vinyl sections loose and retrieving these sections to the mill nip. The stock is then sheeted off thicker than 0.32 cm.

The stock is then press-molded in a 27.9 cm × 27.9 cm × 0.32 cm picture-frame mold to remove bubbles; the stock is first molded at 154° C. (1.5 minutes preheat, 1 minute of pressure 50 tons; 1 minute in cold press). The molded slab is cut in 4 parts, stacked, and remolded 166° C. to achieve a smooth surface.

The sheets are cut into 0.86 cm strips and made into collars approximately 53.5 cm long, weighing about 20 grams.

EXAMPLE 2

Preparation of PVC-Spiro[cyclopropane-1,1'-indene]-2-carboxylic acid, 3,3-dimethyl-, α-cyano-m-phenoxybenzyl ester composition By the procedure of Example 1, the following composition is prepared. The ingredients and amounts are listed below.

| | |
|---|---|
| Diamond PVC 40 | 43.9 g |
| Dioctyl phthalate | 25.0 g |
| Thermolite 831 — di-n-octyltin maleate polymer | 0.9 g |
| Spiro[cyclopropane-1,1'-indene]-2-carboxylic acid, 3,3-dimethyl-, α-cyano-m-phenoxybenzyl ester; 82.5% pure | 30.0 g (24.75 g real) |

EXAMPLE 3

Evaluation of the efficacy of tick collars containing spiro[cyclopropane-1,1'-indene]-2-carboxylic acid, 3,3-dimethyl-, α-cyano-m-phenoxybenzyl ester

Animals

Nine mongrel dogs are randomly distributed into three groups of three dogs each. The animals are housed in cages fitted with a grated floor. Purina High Protein Dog Meal is fed once daily and water offered ad libitum.

Materials and Methods

One group of three dogs serves as unmedicated infested controls.

The dogs in the other groups are fitted with PVC collars 0.86 cm wide, 0.32 cm thick by 50.8 cm long, prepared from the compositions of Examples 1 and 2.

Each dog is infested with 10 male and 10 female adult *Dermacentor variabilis* and *Rhipicephalus sanguineus* on days one, four and seven pretreatment. The collar and the dog are weighed separately to determine the total mg/kg dose rate.

Each dog is observed daily for signs of tick mortality and/or repellency. Numbers of adult ticks falling from treated and control dogs are recorded on an individual basis and oviposition and hatch rates are checked.

Each dog is reinfested weekly after the initial treatment to determine the effective control period for each set of collars. cl Results One week after wearing the collars, both treated and control groups are still infested with ticks, although the treated dogs had reduced tick populations.

All dogs are reinfested with ticks one week after wearing the collars. The tick population on all the treated dogs is low and only one of the treated dogs (fitted with a collar prepared from the Example 2 formulation) has a significant population of young adults four days after reinfestation.

All dogs are reinfested with ticks at one week intervals. Collars prepared from Example 1 composition gave complete tick control. Collars from Example 2 composition were highly effective but failed to give complete control.

The data obtained are summarized in Table I below.

TABLE I

Evaluation of the Efficacy of PVC Animal Collars, Containing Spiro[cyclopropane-1,1'-indene]-2-carboxylic acid, 3,3-dimethyl-, α-cyano-m-phenoxybenzyl ester for the control of Ticks of Dogs.

| Treatment | Dog | Duration of Effectiveness (in Weeks) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Infested, untreated Controls | a | N | N | N | N | N | N | N | N | N | N | N | N |
| | b | N | N | N | N | N | N | N | N | N | N | N | N |
| | c | N | N | N | N | N | N | N | N | N | N | N | N |
| Example 1 | d | P | P | C$_2$ | C | C | P$_3$ | P$_3$ | C | P | N | N | N |
| | e | P | P | C | *P | P$_3$ | N | N | N | N | N | N | N |
| | f | P | P | P | P | C | C | C | C | C | P | C | P |
| | g | | | | | DECEASED | | | | | | | |

TABLE I-continued

Evaluation of the Efficacy of PVC Animal Collars, Containing Spiro[cyclopropane-1,1'-indene]-2-carboxylic acid, 3,3-dimethyl-, α-cyano-m-phenoxybenzyl ester for the control of Ticks of Dogs.

| Treatment | Dog | Duration of Effectiveness (in Weeks) | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Example 2 | h | P | N | P | N | N | $P_3$ | C | P | P | $C_3$ | C | P |
| | i | P | P | P | $C_4$ | $C_5$ | $C_4$ | P | $C_3$ | P | $C_3$ | C | C |

N = no control
P = partial control
C = Control
*Collar destroyed
Subscript (e.g. $C_2$; $P_4$) indicates the number of days past reinfestation, after which the degree of control indicated, is regained.

EXAMPLE 4

Preparation of PVC-0,0,0,',0'-tetramethyl 0,0'-thiodi-p-phenylene phosphorothioate resin composition Diamond 40 PVC resin (1000 g), inherent viscosity 0.80 determined by A.S.T.M. D1243-58T (Method A), weight average molecular weight 120,000 (number average molecular weight 50,000), is charged to a Henschel mixer along with stearic acid (5 g), carbon black (2 g) and Thermolite 831-di-n-octyltin maleate polymer PVC heat stabilizing agent (20 g). The mixer is run at high speed (3600 rpm) until the temperature of the mixture is 79° C., 0,0,0,',0'-tetramethyl 0,0'-thiodi-p-phenylene phosphorothioate (930 g; 90% real) is then added and mixing is continued.

When addition of the phosphorothioate is completed and the temperature of the mixture reaches 93° C., the speed of mixing is reduced to 1800 rpm and the batch discharged. The hot dry blend is then cooled and ready for extrusion.

The extrusion composition is then charged to the feed hopper of the extruder and extruded through a horizontal ribbon die having a 9.52 mm (⅜") wide slot 3.17 mm (⅛") thick.

Extrusion is accomplished with the mixture heated from 121° C. at the rear feed to 165° C. at the die zone and an extruded stock temperature of 163° C. This extrusion is conducted with a head pressure of 21 kg cm$^{-2}$. Circulating water is used to cool the feed throat under the feed hopper as well as the extrudate exiting the die.

The extruded strip is then cut into 61 cm (2') lengths to which a buckle is attached.

The animal collars thus prepared contain only the above-mentioned phosphorothioate which amounts to 42.8% (47.5% as is) by weight of composition.

EXAMPLE 5

0,0,0',0'-Tetramethyl 0,0'-thiodi-p-phenylene phosphorothioate Flea collar activity against Ctenocephalides felis on dogs Two groups of 4 dogs each are infested with 100 adult Ctenocephalides felis three days prior to placing a flea collar around the neck of each dog in one of the groups. The dogs in the second group serve as infested untreated controls. Each dog is systematically examined daily for fleas presence or absence. Complete flea control observed within one week from the time the collar is placed on the dog is considered effective control. Each dog is reinfested weekly with 100 aduct C. felis and examined daily thereafter for fleas. Effective control is considered complete control of C. felis on all dogs within one week of reinfestation.

All dogs are fed Purina High Protein Dog meal once daily and all are provided with water ad libitum. The dogs are housed in individual cages with grate bottom floors.

The data obtained in this example indicate that the flea collar prepared from Example 4 PVC resin-siphonaptericide composition provides complete (100%) control of Ctenocephalides felis for at least 52 weeks.

EXAMPLE 6

Evauation of the efficacy of tick and flea collars in physical combination for simultaneous control of ticks and fleas Animals Four mongrel dogs are used in the test. The animals are housed in cages fitted with grated floor. Purina High Protein Dog Meal is fed once daily and water offered ad libitum.

Material and Methods

One group of two dogs serves as unmedicated infested controls (dogs A & B).

One dog is fitted with two PVC collars, one containing 30% by weight of spiro[cyclopropane-1,1'-indene]-2-carboxylic acid, 3,3-dimethyl-, α-cyano-mphenoxybenzyl ester (prepared by the process of Example 1 ) and the other containing 40.7% by weight of 0,0,0',0'-tetramethyl 0,0'-thiodi-p-phenylene phosphorothioate (prepared by the process of Example 4) (dog C); and one dog is fitted with a Hartz "2 in 1" ®collar, containing 9.5% by weight of 2-chloro-1-(2,4,5-trichlorophenyl)- vinyl dimethyl phosphate (dog D).

Each dog is infested with 10 male and 10 female Dermacentor variabilis and Rhipicephalus sanguineus and with 100 Ctenocephalides felis on days one, four and seven pretreatment.

Each dog is observed daily for signs of tick and flea mortality and/or repellency. Number of adult ticks falling from treated and control dogs are recorded on a individual basis and oviposition and hatch rates are checked.

Each dog is reinfested weekly after the initial treatment to determine the effective control period for each set of collars.

The data obtained are summarized in Table II below.

TABLE II

Evaluation of the Efficacy of Tick and Flea Collars in Physical Combination for the Simultaneous Control of Ticks and Fleas on Dogs, Compared to a Commercial Tick and Flea Collar.

| Treatment | Dog | Insect Tested | 1 | 2 | 3 | 4 | 5 | 6 | 7 | 8 | 9 | 10 | 14 |
|---|---|---|---|---|---|---|---|---|---|---|---|---|---|
| Infested, untreated controls | A | Flea | + | + | + | + | + | + | + | + | + | + | |
| | | Tick | + | + | + | + | + | + | + | + | + | + | |
| | B | Flea | + | + | + | + | + | + | + | + | + | + | + |
| | | Tick | + | + | + | + | + | + | + | + | + | + | + |
| Spiro[cyclopropane-1,1'-indene]-2-carboxylic acid, 3,3-dimethyl-, α-cyano m-phenoxybenzyl ester in combination with 0,0,0',0'-tetramethyl 0,0'-thiodi-p-phenylene-phosphorothioate | C | Flea | − | − | − | − | − | − | − | − | ± | − | − |
| | | Tick | + | − | − | − | − | − | − | − | + | + | + |
| Hartz "2 in 1"® Collar | D | Flea | − | − | − | − | ± | + | + | + | + | | |
| | | Tick | + | ± | ± | ± | + | + | + | + | + | + | |

+ = Few, if any dead
± = Some dead (about 50% +)
− = All dead, or moribund.

It can be seen from the above Table, that the physical combination of two collars, one containing spiro[cyclopropane-1,1'-indene]-2-carboxylic acid, 3,3-dimethyl-, α-cyano-m-phenoxybenzyl ester, and the other 0,0,0',0'-tetramethyl 0,0'-thiodi-p-phenylene phosphorothioate, respectively, offers positive control of fleas and ticks on dogs for 8 weeks. The commerical dog collar, on the other hand, offers only 5 weeks of positive control of fleas and 4 weeks of partial control of ticks, on dogs.

Example 7

Preparation of PVC-Spiro[cyclopropane-1,1'-indene]-2-carboxylic Acid, 3,3-Dimethyl, α-Cyano-m-phenoxybenzyl Ester Composition.

Diamond PVC 40 resin, inherent viscosity approximately 0.80, approximate weight average molecular weight 120,000 is mixed and thoroughly blended with varying amounts of a plasticizer selected from dioctyl phthalate, octyl epoxytallate and 0,0,0',0'-tetramethyl 0,0'-thiodi-p-phenylene phosphorothioate; di-n-octyltin maleate polymer, a heat stabilizing agent for polymers and stearic acid as a lubricating agent. After blending, the compositions are sheeted on a 143° C. two-roll rubber mill. The stock is mixed for 5 minutes by cutting vinyl sections loose and returning these sections to the mill nip. The stock is then sheeted off thicker than 0.32 cm.

The stock is then press-molded in a 27.9 cm × 27.9 cm × 0.32 cm picture-frame mold to remove bubbles; the stock is first molded at 154° C. (1.5 minutes to preheat, 1 minute of pressure, 50 tons); stacked, and remolded at 166° C. to achieve a smooth surface. The sheets are cut into 0.86 cm strips and made into collars approximately 53.5 cm long, weighing about 20 grams.

Physical characteristics of the various preparations are examined and evaluated for acceptability and usefulness. Data obtained are reported below in Table III.

TABLE III

Physical Characterization of Resin Compositions and Acceptability Thereof for Use in the Preparation of Tick-free Animal Collars

| Compound | % by Weight Composition | | | | | | | |
|---|---|---|---|---|---|---|---|---|
| | A | B | C | D | E | F | G | H |
| Spiro[cyclopropane-1,1'-indene]-2-carboxylic acid, 3,3-dimethyl-, α-cyano-m-phenoxybenzyl ester | 30 | 30 | 30 | 30 | 30 | 30 | 20 | 22.8 |
| Dioctyl phthalate | 7.5 | 15 | 20 | 25 | | | | |
| Octyl epoxytallate | — | | | | 20 | 15 | | |
| 0,0,0',0'-Tetramethyl 0,0'-thiodi-p-phenylene phosphorothioate | — | | | | | | 30 | 34.2 |
| Di-n-octyltin maleate polymer | 1.2 | 1.1 | 1.0 | 0.9 | 1.0 | 1.1 | 1.0 | 0.84 |
| Stearic acid | 0.3 | 0.27 | 0.24 | 0.22 | 0.24 | 0.27 | 0.24 | 0.21 |
| Polyvinyl chloride Wt. Avg. Mole. W. 120,000 | 61 | 53.63 | 48.76 | 63.88 | 48.76 | 53.63 | 48.76 | 41.95 |
| Physical characterization | much too stiff | stiff | good, soft | good, soft | good, soft | good, but stiff | too stiff | stiff |
| Acceptability | not acceptable | barely acceptable | acceptable | acceptable | acceptable | barely acceptable | not acceptable | barely acceptable |

From the results of Example 7 above, it can be seen that the composition of Collar A, which contained 7.5% by weight of dioctyl phthalate, was too stiff and unacceptable. Collar B contained 15% by weight of dioctyl phthalate and was barely acceptable, because it was stiff. Collar C with 20% by weight, and Collar D with 25% by weight of dioctyl phthalate, were both soft and very pliable. Collar D was, of course, much more pliable than Collar C and was approaching the unacceptable softness level.

Collar E was soft and acceptable. This collar contained 20% by weight of octyl epoxytallate. Collar F, which contained 15% by weight of octyl epoxytallate, was much stiffer than Collar D and was approaching the unacceptable level of stiffness.

Collar G, which contained 20% by weight of spiro[cyclopropane-1,1'-indene]-2-carboxylic acid, 3,3-dimethyl-, α-cyano-m-phenoxybenzyl ester and 30% by weight of 0,0,0', 0'-tetramethyl 0,0'-thiodi-p-phenylene phosphorothioate, was too stiff to be acceptable. Collar H contained 22.8% by weight of the spiro compound and 34.2% by weight of the phosphorothioate. This collar was very stiff and barely acceptable.

EXAMPLE 8

To determine the effectiveness of the compositions of Example 7, above, for controlling ticks and fleas on dogs, three groups of three dogs each were infested 20 *Dermacentor variabilis* and 20 *Rhipicephalus sanguineus* three times, and 100 *Ctenocephalides felis* once before the animals were fitted with one of the selected collars from said Example 7. Collars D, E and H were selected, because they exhibited the most desirable physical characterisitics in each of their respective groups; said groups being determined on the basis of the plasticizing agent.

Collar D contained 30% by weight of spiro [cyclopropane -1,1'-indene]-2-carboxylic acid, 3,3-dimethyl, α-cyano-m-phenoxybenzyl ester and 25% by weight of dioctyl phthalate; Collar E contained 30% by weight of the abovesaid spiro compound and 20% by weight of octyl epoxytallate, and Collar H contained 22.8% by weight of the spiro compound and 34.2% by weight of 0,0,0',0'-tetramethyl 0,0'-thiodi-p-phenylene phosphorothioate.

Three dogs served as infested, non-treated controls. All animals were reinfested weekly with the same number of fleas and ticks.

One week after wearing the collars, treated and control dogs were still infested with fleas and ticks, although the treated dogs had reduced tick populations. One exception was a dog wearing a composition H collar, which had complete flea control after one week.

All dogs were reinfested with ticks and fleas one week after wearing the collars. All dogs, except one wearing a composition H collar, had fleas 7 days after reinfestation. The tick populations on all treated dogs were very low, and only one of the treated dogs (composition D collar) had a significant population of young adults 4 days after reinfestation.

All dogs were reinfested with ticks and fleas two weeks after wearing the collars. All three dogs wearing composition H collars were completely free of fleas within 7 days after treatment. Fleas were not controlled with composition D or E collars. Composition E collars, however, gave *complete tick control on all dogs within seven days after reinfestation.* Composition D and H collars were highly effective in controlling reinfestation ticks, but did not give complete control within seven days.

From this example it is evident that the selection and amount of plasticizing agent, i.e. 15% to 25% of dioctyl phthalate or octyl epoxytallate, employed in the preparation of animal collars containing the spiro[cyclopropane-1,1'-indene]-2-carboxylic acid, 3,3-dimethyl-, α-cyano-m-phenoxybenzyl ester are essential in providing (1) proper physical characteristics for the animal collars, and (2) effective tick control obtainable therewith.

I claim:

1. A flexible collar for controlling acarina on companion animals comprising: a flexible strip of an acaricidally dry blended polyvinyl chloride resin composition containing from 48% to 66% of a polyvinyl chloride resin having an approximate average molecular weight of 120,000 and an inherent viscosity of about 0.80, from 18% to 35% of spiro[cyclopropane-1,1'-indene]-2-carboxylic acid, 3,3-dimethyl-,α-cyano-m-phenoxybenzyl ester, from 15% to 25% of a plasticizer selected from the class consisting of dioctyl phthalate and octyl epoxytallate, from 0.1% to 0.5% of stearic acid lubricant, and from 0.5% to 1.5% of di-n-octyltin maleate polymer stabilizing agent, said percentages being by weight based on the overall said composition.

2. A flexible collar according to claim 1, for controlling ticks on companion animals, wherein the plasticizing agent is octyl epoxytallate and is 15% to 20% of the resin composition.

3. A flexible collar according to claim 1, for the control of ticks on companion animals, wherein the plasticizing agent is dioctyl phthalate and is 20% to 25% of the resin composition.

4. A flexible collar according to claim 1, for controlling *Rhipicephalus sanguineus* and *Dermacentor variabilis* on dogs.

5. A method for the prolonged control of acarina on dogs and cats comprising employing a flexible collar of a composition of claim 1 around the neck of the dog or cat which is to be protected against acarina infestation or reinfestation.

6. A method for the prolonged control of acarina on dogs and cats comprising using a flexible collar of a composition of claim 2 around the neck of the dog or cat which is to be protected against acarina infestation or reinfestation.

7. A method for the prolonged control of acarina on dogs and cats comprising utilizing a flexible collar of a composition of claim 3 around the neck of the dog or cat which is to be protected against acarina infestation or reinfestation.

8. A method for controlling ticks and fleas on dogs and cats comprising utilizing either two polyvinyl chloride, side by side, collars around the necks of said dogs or cats, one collar containing as defined by claim 1, spiro[cyclopropane-1,1'-indene]-2-carboxylic acid, 3,3-dimethyl-, α-cyano-m-phenoxybenzyl ester and the other containing 0,0,0',0'-tetramethyl 0,0'-thiodi-p-phenylene phosphorothioate, or a single overall collar prepared by laminating the above-said two side by side collars into a single unit.

* * * * *